United States Patent [19]

Kita et al.

[11] 4,088,555
[45] May 9, 1978

[54] OXYGEN SENSOR PARTICULARLY FOR USE IN EXHAUST SYSTEM OF AUTOMOTIVE ENGINE

[75] Inventors: Toru Kita; Takeshi Fujishiro, both of Yokohama, Japan

[73] Assignee: Nissan Motor Company, Limited, Yokohama, Japan

[21] Appl. No.: 731,110

[22] Filed: Oct. 8, 1976

[30] Foreign Application Priority Data

Oct. 9, 1975 Japan .................................. 50/121362
Feb. 12, 1976 Japan .................................. 51/13254

[51] Int. Cl.² ............................................. G01N 27/46
[52] U.S. Cl. ............................... 204/195 S; 123/119 C
[58] Field of Search ............................ 204/15, 195 S; 123/119 E

[56] References Cited

U.S. PATENT DOCUMENTS

| | | | |
|---|---|---|---|
| 3,642,599 | 2/1972 | Franz | 204/195 S |
| 3,841,987 | 10/1974 | Friese et al. | 204/195 S |
| 3,844,920 | 10/1974 | Burgett et al. | 204/195 S |
| 3,847,778 | 11/1974 | Riddel | 204/195 S |
| 3,960,692 | 6/1976 | Weyl et al. | 204/195 S |
| 3,960,693 | 6/1976 | Weyl et al. | 204/195 S |
| 4,019,974 | 4/1977 | Weyl et al. | 204/195 S |

FOREIGN PATENT DOCUMENTS

| | | | |
|---|---|---|---|
| 2,344,245 | 3/1975 | Germany | 204/195 S |
| 2,460,113 | 10/1975 | Germany | 204/195 S |

*Primary Examiner*—T. Tung
*Attorney, Agent, or Firm*—Bacon & Thomas

[57] ABSTRACT

A solid electrolyte tube closed at one end and two porous electrode layers respectively coated on the outer and inner surfaces of the electrolyte tube constitute a known oxygen concentration cell. A tubular metal shell encloses the electrolyte tube partly such that a closed end portion of the tube protrudes from the shell and that the outer electrode coating is locally in contact with the inside of the shell, and a metal tube is partly and fixedly inserted into the bore of the electrolyte tube to serve both as an inner conductor and as an air admitting conduit. To protect the open end of the electrolyte tube against splashing of water during use, an annular ceramic pad is placed on the open end face of the electrolyte tube allowing the metal tube to pass therethrough, and a tubular cap which is shaped to tightly sheathe the ceramic pad is fixed at one end to the shell to prevent the ceramic pad from parting from the end face of the electrolyte tube.

13 Claims, 5 Drawing Figures

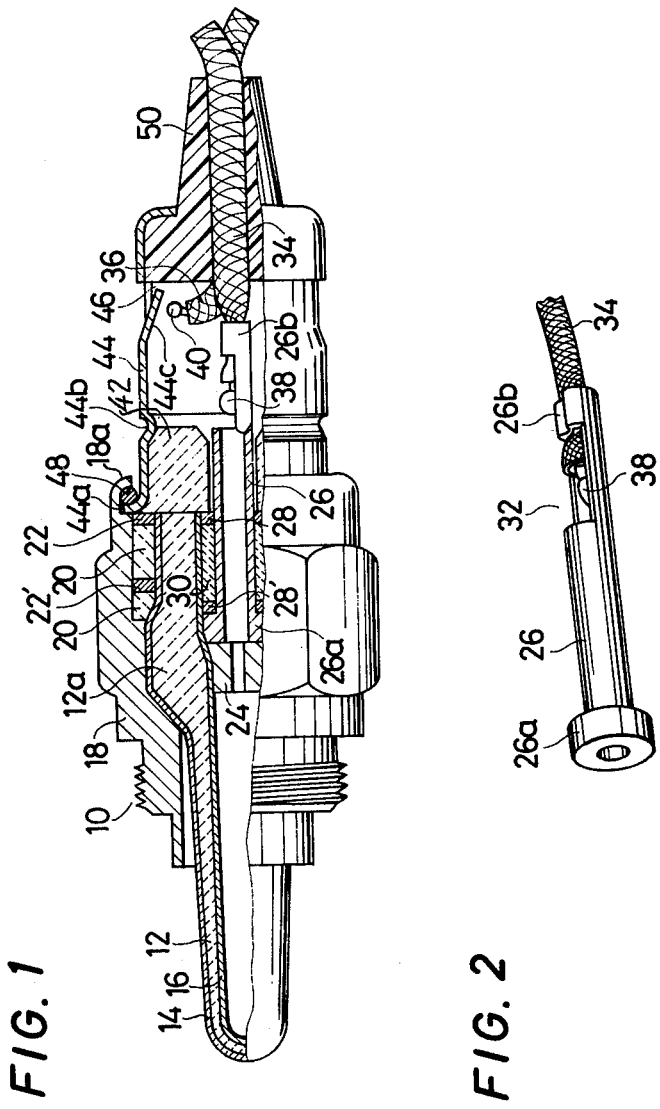

OXYGEN SENSOR PARTICULARLY FOR USE IN EXHAUST SYSTEM OF AUTOMOTIVE ENGINE

This invention relates to an oxygen sensor for detecting oxygen concentration in hot gases, which sensor utilizes an ion conductive solid electrolyte in the form of a tube closed at one end and has a construction particularly suitable for use in exhaust systems of automotive engines.

An oxygen sensor which has a layer of an ion conductive solid electrolyte such as, for example, stabilized zirconia and operates on the principle of an oxygen concentration cell is well known. This type of oxygen sensor is suitable for detecting oxygen concentration in hot gases, particularly in exhaust gases of internal combustion engines for, chiefly, automotive uses as an element of a feedback control system for controlling the air-fuel ratio of a combustible mixture fed to the engine.

In practical applications of oxygen sensors of this type to exhaust systems of internal combustion engines, the solid electrolyte layer in most cases is formed into the shape of a tube which is closed at one end for convenience of attachment to either exhaust manifolds or exhaust pipes for the engines and exposure of the solid electrolyte layer at its one side to the exhaust gas and at the opposite side to the atmospheric air as a reference gas. The outer and inner surfaces of the solid electrolyte tube are coated with porous and electron conductive layers of a catalytic metal, typified by platinum, respectively as the anode and cathode electrodes of the oxygen concentration cell. This solid electrolyte tube is tightly inserted into a tubular metal shell such that a closed end portion of the tube protrudes from the shell. This shell has at its outside a connection or attachment means such as a screw thread for attachement of the sensor to the engine exhaust system and, besides, serves as an anode conductor, A metal tube is inserted into the solid electrolyte tube from its open end to serve both as a cathode conductor and as an air admission conduit. The shell and the inner metal tube are held on position by, for example, shaping the solid electrolyte tube to have locally expanded outer and inner diameters, forming a flange on the inner metal tube and using suitable retainer rings.

When the solid electrolyte tube is assembled with the shell and the inner metal tube, the outer and inner conductive coatings on the solid electrolyte tube are almost inevitably spaced from the shell and the inner metal tube, respectively, at end regions close to the open end of the electrolyte tube. To prevent a leakage of the exhaust gas along the outer conductive coating and assure the electrical connection, the annular space formed between the solid electrolyte tube and the shell is filled with a conductive and heat-resistant sealing agent. The space between the solid electrolyte tube and the inner metal tube is filled with the same sealing agent, too. In conventional oxygen sensors of the described construction, this sealing agent is selected from (a) graphite powder, (b) mixtures of a metal powder such as copper, iron or nickel powder and a refractory but nonconductive powder material such as alumina, magnesia or talc, and (c) semiconducting glasses. In the case of the employment of the material (a) and (b), the powdery seal material is tamped in the above described annular spaces with the support of retainer rings. The material (c) is fused at or subsequently to the filling.

Conventional oxygen sensors of the above described construction has some shortcomings as a device attached to a component of the exhaust line of an automotive engine. (1) Since the solid electrolyte tube is left uncovered at its open end, the electrolyte tube chances to break when the open end is splashed with water while the tube is maintained at a high temperature (usually about 400°-600° C) by the heat of the exhaust gas. (2) The fixing of the solid electrolyte tube to the shell and the inner metal tube to the electrolyte tube is accomplished by means of retainer rings which are made of a soft metal such as copper, but the rings tend to lose their resilient property or retaining ability during a prolonged use of the sensor together with the engine, resulting in looseness of the fixing, particularly of the inner metal tube to the electrolyte tube. The average life of these oxygen sensors, therefore, is shorter than that of the exhaust system component to which they are attached. Besides, the conductive sealing agent closedly filled in the spaces between the shell and the electrolyte tube often exhibits degradation in its sealing and/or conducting properties as the result of heat transfer from the exhaust gas and practically inevitable contact with the exhaust gas which contains oxidizing and corrosive components. Graphite as the sealing agent is gradually oxidized and diminishes in its volume upon continual contact with the exhaust gas at temperatures above about 500° C, resulting in loosening or partial crumbling of the tamped sealing agent which undergoes mechanical vibrations during the operation of the engine. When a powdery mixture containing a metal powder is employed as the sealing agent, the electrical conductivity of the agent gradually lowers as the metal powder undergoes gradual oxidation upon long exposure to high temperatures. A semiconducting glass filled in the space is liable to crack by experience of repeated heating and cooling cycles and exhibits a lowering in its sealing ability.

It is an object of the present invention to remedy these shortcomings of conventional oxygen sensors of the above described type.

It is another object of the invention to provide an improved oxygen sensor which has an improved resistance to the splashing of water, improved durability under severe operational conditions involving high temperatures and mechanical vibrations and improved reliability in electrical connections and, accordingly, is particularly suitable for use in the exhaust system of an automotive internal combustion engine.

An oxygen sensor according to the invention, like conventional oxygen sensors of the above described type, has tubular metal shell, an ion conductive solid electrolyte tube which is closed at one end and is inserted into the shell such that a front portion of the electrolyte tube including the closed end protrudes from the shell, a porous and conductive first electrode layer formed on and in intimate contact with the outside of the electrolyte tube to locally be in contact with the inside of the shell, a porous and conductive second electrode layer formed on and in intimate contact with the inside of the electrolyte tube, and a metal tube inserted into the electrolyte tube to locally be in contact with the second electrode layer and partly extend outwards from the open end of the electrolyte layer thereby to serve both as an electrical conductor and a conduit for admitting the atmospheric air into the interior of the electrolyte tube. According to the invention, the oxygen sensor further comprises an annular pad of an electrically nonconductive ceramic material which has an outer diameter larger than that of the open end of the electrolyte tube and an inner diameter smaller than that of the open end of the electrolyte tube but larger than the outer diameter of the metal tube and is arranged substantially coaxially with the electrolyte tube to at one end face be in contact with and cover the open end face of the electrolyte tube and enclose a portion of the metal tube, and a tubular cap fixed at one end portion to the shell and so shaped as to tightly sheathe the pad and prevent the pad from parting from the open end face of the electrolyte tube.

Preferably, the cap has a flange at one end surrounding the front end of the pad contacted with the open end of the electrolyte tube and an annular ridge formed on the inside to support the rear end of the pad, and an end portion of the shell is made to extend from the open end of the electrolyte tube with an inner diameter larger than the flange of the cap and is crimped inwards with a seal ring placed on the outside of the cap to be compressed against the flange.

To fix the shell to the electrolyte tube and assure the electrical connection between the shell and the first electrode layer, preferably and in a known manner, the shell is made to be in contact with the first electrode layer at a distance from the open end of the electrolyte tube and have an inner diameter large enough to provide an annular space around a rear portion of the electrolyte tube including the open end, and the annular space is filled with a powdery and electrically conductive sealing agent and a metal ring forcibly inserted into the annular space to be in contact with both the first electrode layer and the inside of the shell and prevent the discharge of the sealing agent from the annular space. As a subsidiary feature of the invention, the sealing agent in the annular space takes the form of a plurality of annular layers which consist of at least one first seal layer of a powdery, refractory and electrically non-conductive material and at least one second seal layer of a powdery and electrically conductive material in a columnar and alternate arrangement, wherein an end portion of the annular space closest to the closed end of the electrolyte tube is filled with the first seal layer.

Examples of the material of the first seal layer are alumina, magnesia, talc and kaolin. The material of the second seal layer is selected from graphite, metals such as copper, iron and nickel, semiconducting metal oxides such as NiO, $Ni_2O_3$, CuO, ZnO, $Fe_2O_3$ and CoO, semiconducting oxides of the perovskite structure and their mixtures with each other or the above listed refractory materials.

The electrolyte tube in the oxygen sensor according to the invention is fully protected against cracking by the splashing of water while the sensor is used in motor vehicles and exposed to a high temperature exhaust gas since the ceramic pad completely and practically airtightly covers the open end of the electrolyte tube. The fixing of the tubular cap to the shell and the compression of the ceramic pad against the electrolyte tube are effective in preventing the occurrence of loosening in the assembled sensor. The multi-layer structure of the sealing agent with a refractory and nonconductive layer at the front end has the advantage that the conductive component of the sealing agent is effectively protected against oxidation.

The invention will fully be understood from the following detailed description of preferred embodiments, in comparison with a conventional oxygen sensor, with reference to the accompanying drawings, wherein:

FIG. 1 is a longitudinal sectional view of an oxygen sensor according to the invention;

FIG. 2 is an enlarged perspective view of a part of the sensor of FIG. 1;

Figure 3:
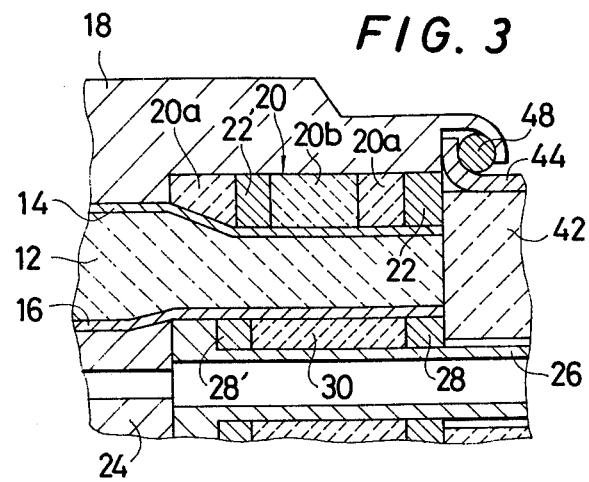
FIG. 3 is a fragmentary enlargement of FIG. 1.

An oxygen sensor 10 of FIG. 1 according to the invention operates on the known principle of an oxygen concentration cell: the sensor 10 has a layer in the form of a tube 12 of an oxygen-ion conductive solid electrolyte typified by a zirconia ceramic containing calcia as a stabilizing oxide. The solid electrolyte tube 12 is closed at one end (this end will hereinafter be referred to also as the front end of the solid electrolyte tube and the open end as the rear). The outer surface of the solid electrolyte tube 12 is entirely coated with a porous and electron conductive anode electrode layer 14. For detecting oxygen concentration in the exhaust gas of an internal combustion engine, this electrode layer preferably has a catalytic activity on the oxidation of oxidizable components of the exhaust gas and is usually made of platinum. The inner surface of the solid electrolyte tube 12 is entirely coated with a cathode electrode layer 16 which is usually similar to the anode electrode layer 14 both in the material and in the structure.

The outer diameter of the solid electrolyte tube 12 is locally enlarged to form an annular ridge or collar 12a between a middle section and the open end of the tube 12. The solid electrolyte tube 12 is inserted into a tubular metal shell 18 the inner diameter of which is locally enlarged to fit with the collar 12a of the electrolyte tube 12 such that a front end portion of the electrolyte tube 12 protrudes from the metal shell 18. This metal shell 18 has on its outside an attachment means such as a screw thread to airtightly insert the protruded portion of the electrolyte tube 12 into and through the wall of either the exhaust pipe or the exhaust manifold for the engine. The metal shell 18 serves also as an anode conductor. The solid electrolyte tube 12 and the metal shell 18 are so shaped as to provide an annular space therebetween at a region from the rear end of the collar 12a to the rear end of the electrolyte tube 12. This annular space is filled with a powdery and electrically conductive sealing agent 20, which has been closely packed. To support the sealing agent 20 and fix the solid electrolyte tube 12 to the metal shell 18, a ring 22 of a relatively soft metal such as copper is forcibly inserted into the rear end portion of the annular space. This ring 22 contributes also to the assurance of electrical connection between the anode coating 14 and the metal shell 18. Another copper ring 22' may be forcibly inserted into a middle portion of the annular space to divide the sealing agent 20 into two blocks when the annular space has a relatively large axial length.

A rear end portion of the bore of the solid electrolyte tube 12 is made to have an enlarged diameter with a tapered section at the inside of the collar 12a, and a copper ring 24 having a tapered periphery at its rear end portion is inserted into the bore of the electrolyte tube 12 to fit with the tapered region of the bore. A metal tube 26 which has a flange 26a at one end sized to closely fit with the inside (to be exact, the cathode coating 16) of the enlarged portion of the electrolyte tube 12 is inserted into the rear portion of the electrolyte tube 12 such that the flange 26a comes into contact with the copper ring 24. This metal tube 26 has such a length that its rear end portion remains outside the bore of the electrolyte tube 12. An annular space formed in the rear of the flange 26a between the cathode coating 16 and the metal tube 26 is filled with a powdery and electrically conductive sealing agent 30, which has been tamped, and copper rings 28 and 28' which are forcibly inserted into the space to retain the sealing agent 30 in the tamped state and assure the electrical connection between the cathode coating 16 and the metal tube 26. Thus, the metal tube 26 serves both as a cathode conductor and as a conduit for admitting air as a reference gas into the interior of the electrolyte tube 12.

The metal tube 26 has a slot 32 in the rear end portion protruding from the electrolyte tube 12 at a short distance from the rear end of the metal tube 26 as seen in FIG. 2. A jacketed cable wire 34 to serve as the cathode lead of the sensor 10 is inserted into the metal tube 26 from its rear end, and the uncut (accordingly tubular) end portion 26a of the metal tube 26 is squeezed to firmly clamp the cable 34 with its jacket unstripped. The inserted end of the cable 34 is stripped and either welded or soldered to the inside of the metal tube 26 as indicated at 38 by the use of the slot 32.

As a primary feature of the sensor 10 according to the invention, an annular ceramic pad 42 is substantially coaxially attached to the exposed rear end face of the solid electrolyte tube 12. This ceramic pad has an outer diameter larger than that of the rear (open) end of the electrolyte tube 12 and an inner diameter smaller than that of the rear end of the electrolyte tube 12 but larger than the outer diameter of the metal tube 26. Accordingly, the metal tube 26 is locally enclosed in the ceramic pad 42 with a very narrow annular space therebetween. Both the rear end face of the electrolyte tube 12 and the front end face of the ceramic pad 42 are made flat to realize a close contact with each other. The annular pad 42 is made of a conventional electrically nonconductive ceramic material which may contain alumina and/or silica as its fundamental component.

The ceramic pad 42 should be held stationary in the above described position in any manner. In the illustrated sensor 10, a tubular cap 44 made of a sheet metal sheathes the ceramic pad 42, and the metal shell 18 has a thin-wall rear end portion 18a extending rearwards of the rear end of the electrolyte tube 12 for fixing the cap 44 to the shell 18. The cap 44 is bent outwards at its front end portion to provide a flange 44a which covers the rear end of the annular space between the shell 18 and the anode coating 14. The cap 44 is grooved at its middle section to provide an annular ridge 44b on the inside for supporting the rear end of the ceramic pad 42. A seal ring 48 made of a relatively soft metal is placed on the outside of the cap 44, and the thin-wall end portion 18a of the shell is crimped inwards to press the seal ring 48 against the flange 44a. The two copper rings 22 and 28 are positioned in the respective annular spaces preferably such that the outer end faces thereof are substantially in the same plane as the open end face of the electrolyte tube 12 and, accordingly, are contacted with the ceramic pad 42.

A plurality of slits indicated at 46 are formed in the cap 44 at a certain distance from the rear (free) end of the cap 44 in a circumferential and spaced arrangement. Each of these slits 46 is shaped to consist of two linear and spaced portions extending parallel to the longitudinal axis of the cap 44 and a circumferential portion connecting the two linear portions at their ends closer to the free end of the cap 44. A claw 44c is formed by folding inwards the rectangular region surrounded by each of the slits 46 on three sides. A tubular plug 50 which is made of an elastic and relatively heat-resistant resin such as polytetrafluoroethylene resin is partly inserted into the free end portion the cap 44. A jacketed cable 36 to serve as the anode lead of the sensor 10 are passed through the bore of the plug 50 together with the cathode cable 34. The plug 50 is shaped to have a shoulder on the outside, and the free end of the cap 44 is crimped inwards against the shoulder of the plug 50. The above described claws 44c support the inserted end of the plug 50, so that the plug 50 is fixed to the cap 44 by the crimping of the cap 44. Besides, the gaps between these claws 44c and the unfolded region of the cap 44 serve as air inlet ports of the sensor 10. The inserted end of the anode cable 36 is stripped and connected to the inside of the cap 44 as indicated at 40 either by welding or soldering. The gap between the cables 34 and 36 and the inside of the plug 50 is filled with a usual sealant such as, for example, silicone rubber.

Figure 4:
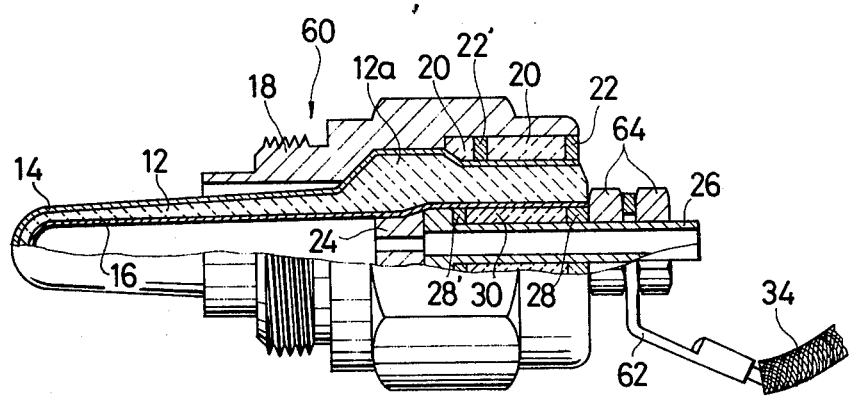
FIG. 4 is a longitudinal sectional view of a conventional oxygen sensor.

The distinctness of the sensor 10 of FIG. 1 will well be understood by comparison with a conventional oxygen sensor 60 shown in FIG. 4, which is based on the same principle. In this oxygen sensor 60, fundamental components such as the solid electrolyte tube 12, the electrode coatings 14, 16, the metal shell 18, the metal tubes 24 and 26, the sealing agents 20 and 30, and the copper rings 22 and 28 are substantially identical with ones in the oxygen sensor 10 of FIG. 1. The sensor 60 has no particular element to cover the open end of the electrolyte tube 12, and the metal tube 26 is neither particularly shaped nor slitted in its rear portion located outside the electrolyte tube 12, but has a screw thread on the outside of this portion. The cathode cable 34 is connected to the metal tube 26 by means of a terminal 62, which is usually a solderless terminal, attached to the end of the cable 34 and two nuts 64 engaged with the thread on the metal tube 26 to firmly hold the terminal 62 therebetween. The anode cable (omitted from FIG. 4) is connected to the metal shell 18 either directly or indirectly.

Since the open end face of the electrolyte tube 12 of the sensor 60 is at least partly exposed to the atmosphere, the electrolyte tube 12 is liable to crack and break by the splashing of external water during the use of the sensor 10 particularly in vehicles. Besides, the fixing of the metal tube 26 to the electrolyte tube 12 (as well as the fixing of the electrolyte tube 12 to the shell 18) solely relies on the forcibly inserted metal rings 28, 28'. Since the metal rings 28, 28' (as well as the metal rings 22, 22') tend to loose their resilience as they are exposed to high temperatures and air, the friction joint between the metal tube 26 and the cathode electrode coating 16 on the inside of the electrolyte tube 12 is liable to loosen during the use of the sensor 60.

In the sensor 10 of FIG. 1, the open end of the electrolyte tube 12 is completely covered by the ceramic pad 42, and the ceramic pad 42 is well protected against the access of a foreign matter such as water by the cap 44 and the plug 50. Accordingly, the electrolyte tube 12 is free from the fear of cracking by the splashing of external water. Besides, the cap 44 is so fixed to the shell 18 as to permanently press the ceramic pad 42 against not only the electrolyte tube 12 but also the metal tube 26 through the metal ring 28. Accordingly, the metal ring 28 has a less chance of deteriorating, and there is little chance that the metal tube 26 becomes loose in the bore of the electrolyte tube 12. The provision of the cap 44 and the plug 50 together with the described shaping of the rear portion of the metal tube 26 has an additional advantage that the cables 34 and 36 can firmly be connected to the sensor 10 and are well protected against damages attributable to, for example, mechanical vibrations and splashing of water.

In the oxygen sensor 10 of FIG. 1, the conductive sealing agent 20 closely packed in the annular space between the shell 18 and the anode coating 14 and the conductive sealing agent 30 closely packed between the metal tube 26 and the cathode coating 16 may be a mixture of a powdery and refractory material typified by alumina powder and a metal powder typified by copper powder as in conventional oxygen sensors. However, we have discovered also that the lowering in the conductivity of the outer conductive sealing agent 20 due to gradual oxidation of the conductive component of the sealing agent 20 during long use of the sensor 10 can be precluded by the employment of a multi-layer structure as will hereinafter be described with reference to FIG. 3.

The outer sealing agent 20 of the multi-layer structure according to the invention has at least one annular refractory layer 20a of a refractory and electrically nonconductive powdery material and at least one annular conductive layer 20b of an electrically conductive powdery material in an alternate and columnar arrangement with no gap between the respective layers 20a, 20b. There is no restriction on the total number of these two types of layers 20a and 20b so long as the two types are both employed. It is necessary that a frontmost portion (the left side in the drawings) portion of the outer sealing agent 20 be occupied by the refractory and nonconductive layer 20a. It is preferable that the conductive layer 20b is sandwiched between the two refractory layers 20a as shown in FIG. 3 (it is permissible that the intermediately positioned metal ring 22' is interposed between the two adjacent and different layers 20a and 20b). Both the refractory layers 20a and the conductive layers 20b are formed by tamping or press-compacting the respective powdery materials in the annular spaces. The refractory layers 20a and the conductive layers 20b may be either identical or individually different in the thickness.

Preferred examples of the material of the refractory layer 20a are alumina, magnesia, talc and kaolin, including their various mixtures. These materials preferably has a mean particle size ranging from about 2 to about 50 μm. Preferred examples of the material of the conductive layer 20b are graphite which may optionally be mixed with a different conductive and/or refractory powder, metals such as copper, iron and nickel, semiconducting metal oxides such as NiO, $Ni_2O_3$, CuO, ZnO, $Fe_2O_3$ and CoO, and oxide semiconductors of the perovskite structure exemplified by $LaAlO_3$ containing Mn, Cr, Co and/or Ni in the form of solid solution. These conductive powdery materials may be used singularly, in various combinations or as a mixture with any of the above described refractory and nonconductive materials.

Figure 5:
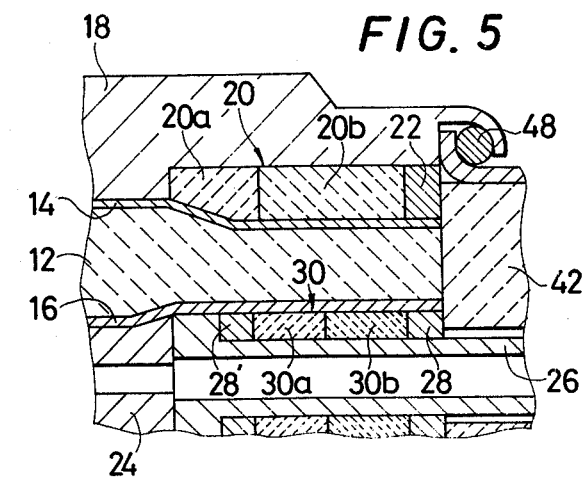
FIG. 5 is a fragmentary sectional view of another oxygen sensor as a slight modification of the sensor of FIG. 1 with regard to a sealing layer shown in FIG. 3.

Since at least the front portion of the outer sealing agent 20 (which portion is most highly heated during the use of the sensor 10) is occupied by the refractory layer 20a, the conductive layer(s) 20b is effectively protected against oxidation. Even when graphite is employed as the material of the conductive layer 20b, there is no fear that the packed graphite is oxidized and that the volume of the packed graphite so diminishes as to cause a lowering in the sealing ability of the sealing agent 20. In practice, it is convenient to employ graphite powder as the material of the conductive layer 20b and a mixture of alumina powder and talc as the material of the refractory and nonconductive layer 20a. The merit of the multi-layer structure is acquired to a practical satisfaction even when the outer sealing agent 20 consists of only one refractory layer 20a occupying a frontmost portion and only one conductive layer 20b as shown in FIG. 5.

The inner sealing agent 30 is not necessarily made to have the above described multi-layer structure since this sealing layer 30 is not directly exposed to the exhaust gas. It is of course permissible, however, that the inner sealing agent 30 consists of alternately arranged at least one refractory and nonconductive layer 30a and at least one conductive layer 30b, as exemplified in FIG. 5, similarly to the outer sealing agent 20.

What is claimed is:

1. In an oxygen sensor particularly for detecting oxygen concentration in the exhaust gas of an automotive internal combustion engine, the sensor having an ion conductive solid electrolyte tube which is closed at one end, first and second porous electrode layers respectively coated on the outer and inner surfaces of the electrolyte tube, a tubular metal shell enclosing therein the electrolyte layer partly such that a closed end portion of the electrolyte tube protrudes from the shell and that the first electrode layer is in contact with the inside of the shell, and a metal tube which is inserted into the bore of the electrolyte tube in contact with the second electrode layer and partially protrudes from the open end of the electrolyte tube thereby to serve both as a conductor and a conduit for admitting air as a reference gas into the interior of the electrolyte tube, the improvement comprising (a) an annular pad of an electrically nonconductive ceramic material which has an outer diameter larger than that of the open end of the electrolyte tube and an inner diameter smaller than that of the open end of the electrolyte tube but larger than the outer diameter of the metal tube and is arranged substantially coaxially with the electrolyte tube such that a front end face of the ceramic pad is in contact with and covers the open end face of the electrolyte tube, and (b) a tubular metal cap which is shaped to tightly sheathe said ceramic pad and so fixed at a front end portion thereof to the shell as to prevent said ceramic pad from parting from the open end face of the electrolyte tube, whereby the open end of the electrolyte tube is protected against access of a foreign matter thereto.

2. An oxygen sensor as claimed in claim 1, wherein said metal cap is shaped to have a flange at said front end portion thereof and an annular ridge formed on the inside thereof at such a location in a middle portion thereof that a rear end of said ceramic pad is supported by said ridge, the sensor further comprising a metal seal ring which has an inner diameter engageable with the outer diameter of said cap and is concentrically placed on the outside of said cap, a rear end portion of said shell being made to have an inner diameter larger than the outer diameter of said flange and extends rearwards from the open end of the electrolyte tube, said rear end portion of the shell being crimped inwards to press said flange against the open end of the electrolyte tube with said seal ring interposed between and in intimate contact with the inside of the crimped end portion of the shell and the flanged region of the outside of said cap.

3. An oxygen sensor as claimed in claim 2, further comprising a tubular plug which has a shoulder on the outside and is partly and tightly inserted into a rear end portion of said cap to close the rear end of said cap and pass cables for the sensor through the bore of said plug, said cap being crimped inwards at the rear end portion to support said shoulder of said plug and having a plurality of claws formed on the inside in a circumferential arrangement between said ridge and said rear end portion to support the inserted end of said plug, each of said claws being formed by forming a curved slit in said cap and pushing inwards a region surrounded by said slit.

4. An oxygen sensor as claimed in claim 3, wherein said metal tube has a slot formed at a rear end portion protruding from the electrolyte tube at a distance from the rear end, so that one of cables for the sensor can be connected to the second electrode layer by inserting the cable into the rear end portion of the metal tube, squeezing the annular region of said metal tube remaining between said slot and the rear end to clamp the cable from the outside of a jacket and joining the inserted end of the cable to the inside of said metal tube by the use of said slot.

5. An oxygen sensor as claimed in claim 1, wherein the electrolyte tube, the shell and the metal tube are respectively shaped such that an outer annular space is formed between the inside of the shell and the first electrode layer around a rearmost portion of the electrolyte tube adjacent the open end, while an inner annular space is formed between the outside of said metal tube and the second electrode layer enclosed in a rearmost portion of the electrolyte tube adjacent the open end, the sensor further comprising a first retainer ring of a metal tightly inserted into said outer annular space to occupy a rearmost portion of said outer annular space, and a second retainer ring of a metal tightly inserted into said inner space to occupy a rearmost portion of said inner annular space.

6. An oxygen sensor as claimed in claim 5, further comprising a powdery sealing agent which is closely packed in said outer annular space and consists of alternately arranged at least one refractory and annular layer of a refractory and electrically nonconductive material and at least one conductive and annular layer of an electrically conductive material, a frontmost portion of said outer annular space closest to the closed end of the electrolyte tube being occupied by said refractory and annular layer.

7. An oxygen sensor as claimed in claim 6, wherein said refractory and electrically nonconductive material is selected from the group consisting of alumina, magnesia, talc and kaolin, including mixtures thereof, while said electrically conductive material is selected from the group consisting of graphite, a metal and a semiconducting metal oxide, including mixtures thereof.

8. An oxygen sensor as claimed in claim 7, wherein said electrically conductive material further comprises said refractory and electrically nonconductive material.

9. An oxygen sensor as claimed in claim 7, wherein said metal as said electrically conductive material is selected from the group consisting of copper, iron and nickel.

10. An oxygen sensor as claimed in claim 7, wherein said semiconducting metal oxide is selected from the group consisting of $NiO$, $Ni_2O_3$, $CuO$, $ZnO$, $Fe_2O_3$, $CoO$ and a semiconducting oxide of the perovskite structure.

11. An oxygen sensor as claimed in claim 7, wherein said refractory layer is of a mixture of alumina and talc, while said conductive layer is of graphite.

12. An oxygen sensor as claimed in claim 11, wherein said sealing agent consists of two layers of said refractory layer and a single layer of said conductive layer.

13. An oxygen sensor as claimed in claim 7, wherein said inner annular space also is filled with said powdery sealing agent.

* * * * *